United States Patent [19]
Burnie et al.

[11] Patent Number: 5,777,083
[45] Date of Patent: Jul. 7, 1998

[54] STRESS PROTEIN EPITOPES

[75] Inventors: James Peter Burnie; Ruth Christine Matthews, both of Wilmslow, Great Britain

[73] Assignee: NeuTec Pharma Plc, United Kingdom

[21] Appl. No.: 387,790

[22] PCT Filed: Aug. 17, 1993

[86] PCT No.: PCT/GB93/01745

§ 371 Date: Apr. 10, 1995

§ 102(e) Date: Apr. 10, 1995

[87] PCT Pub. No.: WO94/04676

PCT Pub. Date: Mar. 3, 1994

[30] Foreign Application Priority Data

Aug. 18, 1992 [GB] United Kingdom .................. 9217542

[51] Int. Cl.$^6$ .................................................. C12P 21/08
[52] U.S. Cl. ................... 530/387.3; 435/7.31; 435/320.1
[58] Field of Search .................... 530/387.3; 435/320.1, 435/7.31

[56] References Cited

U.S. PATENT DOCUMENTS

| | | | |
|---|---|---|---|
| 5,188,964 | 2/1993 | McGuire | 436/64 |
| 5,288,639 | 2/1994 | Burnie et al. | 435/320.1 |
| 5,447,843 | 9/1995 | McGuire | 435/64 |
| 5,474,892 | 12/1995 | Jakob et al. | 435/4 |
| 5,541,077 | 7/1996 | Burnie et al. | 435/7.31 |

FOREIGN PATENT DOCUMENTS

| | | |
|---|---|---|
| 0406029 | 2/1991 | European Pat. Off. |
| WO 91/00351 | 1/1991 | WIPO |
| 9201717 | 2/1992 | WIPO |
| WO 92/01717 | 2/1992 | WIPO |

OTHER PUBLICATIONS

Matthews, R.C., et al., "Autoantibody To Heat-Shock Protein 90 Can Mediate Protection Against Systemic Candidosis," *Immunology*, 1991, vol. 74, pp. 20–24.

Hickey, Eileen, et al., "Sequence And Regulation Of A Gene Encoding A Human 89–Kilodalton Heat Shock Protein," *Molecular And Cellular Biology*, 1989, vol. 9, No. 6, pp. 2615–2626.

Burnie, James P., et al., "Heat Shock Protein 88 And Aspergillus Infection," *Journal Of Clinical Microbiology*, 1991, vol. 29, No. 10, pp. 2099–2106.

Matthews, R.C., "HSP 90, Yeasts And Corynebacterium Jeikeium," *Epidemiology And Infection*, 1991, vol. 107, pp. 273–283.

Matthews, Ruth, et al., "The Application Of Epitope Mapping In The Development Of A New Serological Test For Systemic Candidosis," *Journal Of Immunological Methods*, 1991, vol. 143, pp. 73–79.

Matthews et al. Epiderm. & Infect., 1991, vol. 107, pp. 273–283.

Matthews et al. Immunology, vol. 74, 1991, pp. 20–24.

Jendoubi, M et al. Nucleic Acids Res., vol. 16(22) 1988, p. 10928.

Binart, N. et al. Biochem. Biophys. Res. Comm., 1989, vol. 159(1), pp. 140–147.

Shinnick, T.M. 1991, vol. 167, pp. 145–160, Curr. Top. Microbiol. Inamun.

Lehner, T. et al. Infect & Immun., Apr. 1991, vol. 59(4) pp. 1434–1441.

Hoffmann, T et al. Gene, vol. 74, 1988, pp. 491–501.

Moore, SK et al. J. Biol. Chem., vol. 264(10) Apr. 5, 1989, pp. 5343–5351.

Hickey, E. et al. Mol. & Cell. Bio. Jun. 1989, vol. 9(6), pp. 2615–2626.

Matthews, R.C., J. Med. Microbiol. vol. 36, 1992, pp. 367–370.

Moore, S. K et al. DNA & Cell Bio.,vol. 9(6) 1990, pp. 387–400.

Rebbe, N.F. et al. Gene, vol. 53, 1987, pp. 235–245.

Yamazaki, M et al. Agric. Biol. Chem., vol. 54(12) pp. 3163–3170, 1990.

Yamazaki, M et al. Nucleic Acids Res., vol. 17(17), 1989.

Farrelly, FW et al. J. Analy. Chem., vol. 259(9), May 1984, pp. 5745–5741.

Gaston, JSH. Int. J. Clin. Lab Res., vol. 22, pp. 90–94, 1992.

Kumar, N et al. Infect. Immun. May 1990, vol. 58(5), pp. 1408–1404.

Matteir D et al. J. Immunol. Oct. 1989, vol. 19(10), pp. 1823–1828.

Sharma, D., Comp. Biochem. Physiol., Jul. 1992, vol. 102(3) pp. 437–444.

Ozawa, K et al. Genomics, vol. 12, 1992, pp. 214–220.

Matthews et al. J. of Imm. Methods, vol. 143, 1991, pp. 73–79.

Jung, G et al, Angewandte Chemie, vol. 31(4), Apr. 1992, pp. 367–486.

Geysen, HM et al. J. Mol. Recognit., vol. 1(1), pp. 32–41, Feb. 1988.

Guglielmi, G. et al. J. Bact., Nov. 1991, vol. 173(22), pp. 7374–7381.

*Primary Examiner*—James C. Housel
*Assistant Examiner*—Ginny Allen Portner
*Attorney, Agent, or Firm*—Cushman Darby & Cushman IP Group of Pillsbury Madison & Sutro

[57] ABSTRACT

A functional epitope which is purified from human HSP 90 or which is synthesised to correspond to such a purified epitope, which is, if purified, unchanged or changed by substitution of selected amino acids and if synthesised is identical to a purified epitope or differs from a purified epitope by substitution of selected amino acids, and which cross-reacts with an antibody raised against a stress protein.

12 Claims, No Drawings

STRESS PROTEIN EPITOPES

This invention concerns stress protein epitopes intended inter alia for use in diagnosis and treatment of disease states in which stress proteins are produced.

Environmental stress can induce an increase in the rate of synthesis of so-called heat shock, or stress, proteins in both procaryotic and eucaryotic cells (see for example Schlesinger et al (eds) in: Heat Shock from Bacteria to Man, Cold Spring Harbor, N.Y., (1972)). Although the function of the stress proteins has yet to be finally resolved, some have been reported to participate in assembly and structural stabilisation of certain cellular and viral proteins, and their presence at high concentration may have an additional stabilising effect during exposure to adverse conditions.

Many pathogenic organisms have been shown to produce stress proteins (see Young et al, Proc. Natl. Acad. Sci. USA, 85, 4267–4270 (1988)). The proteins are thought to be produced in response to the stress of infection to help protect the invading pathogen. Thus, for example, the ability to produce stress proteins has been implicated in the survival of bacterial pathogens within macrophages (Christmas et al, Cell, 41, 753–762 (1985) and Morgan et al, Proc. Natl. Acad. Sci. USA, 83, 8059–8063 (1986)).

Burnie et al, (GB 90307236.1, WO 92/01717), have found that stress proteins from both fungi and bacteria, for example, *Candida albicans* and *Corynebacterium leikium*, comprise an immunodominant conserved antigen. The carboxy end of the Candidal stress protein has been sequenced and an antibody raised against the epitope LKVIRKNIVKK-MIE found to recognise both the 47 and 92 Kd Candidal stress proteins in sera from patients suffering from systemic Candidal infection. In addition, the antibodies also recognised stress proteins in sera of patients suffering from other fungal infection, for example, the 40 and 88/84 Kd Aspergillus stress proteins, as well as stress proteins in sera from patients suffering from bacterial infection, for example, the 52 and 86 Kd Coryneform stress proteins. Other peptide sequences from the Candidal stress protein were found to be immunogenic, for example, the epitopes LSREM, LKVIRK and STDEPAGESA reacted with sera from patients with systemic candidiasis.

The entire human 89 kDa heat shock protein (HSP90) gene has been sequenced (Hickey et al, Mol. Cell. Biol., 9, 2615–2626, 1989) and its amino acid sequence deduced and compared to that of heat shock proteins of other species. Although it appears that the class of heat shock proteins is highly conserved among species, direct comparison and identification of common functional sequences (i.e. epitopes) of the heat shock proteins have not been reported.

It is now found that, notwithstanding the efficacy of the earlier described epitopes, routes to production, other than from the carboxy sequence of the candidal HSP90, can give equal or potentially superior results when used in diagnosis or therapy.

According to the present invention there is provided a functional epitope which is purified from human HSP 90 or which is synthesised to correspond to such a purified epitope, which is, if purified, unchanged or changed by substitution of selected amino acids and if synthesised is identical to a purified epitope or differs from a purified epitope by substitution of selected amino acids, and which cross-reacts with an antibody raised against a stress protein.

The epitope may comprise the amino acid sequence XXXLXVIRKXIV, or XXXILXVIXXXXX, wherein X is any amino acid, and may comprise, for example, the amino acid sequence NKILKVIRKNIV.

The epitope may be selected from the amino acid sequences KIRY, NNLGTI, QFIGYPI, KKIK, SKEQV or Candidal equivalent sequence SIKAV, GLELPE or Candidal equivalent sequence FELEES, LDKK or Candidal equivalent sequence LGDQ, WTAN or Candidal equivalent sequence WSAN, NSTMGY or Candidal equivalent sequence TTMSSY, PIVET or Candidal equivalent sequence PIIKE, or KNDK or Candidal equivalent sequence AEDK.

The stress protein may comprise a malarial stress protein, a fungal stress protein or a bacterial stress protein.

The fungal stress protein may comprise a Candidal 92 and/or 47 KDa protein or an Aspergillus 40, 51 and/or 88/84 KDa protein, or a stress protein of *Pneumocystis carnii*.

The bacterial stress protein may comprise a Coryneform 86 and/or 52 KDa protein or a Streptococcal stress protein.

The invention also comprises, in another aspect, a method of making a functional epitope from human HSP 90 or by synthesis, comprising the step of purification from human HSP 90 with or without substitution of selected amino acids or of synthesis of an epitope which is identical to a purified epitope or which differs from a purified epitope by substitution of selected amino acids, the amino acid subsitution being selected so that the epitope cross-reacts with an antibody raised against a stress protein.

The epitope according to the invention is described as a functional epitope and, as such, has a number of functional uses. In particular it may be used in the diagnosis and treatment of a number of diseases as an alternative and/or improvement to conventional diagnostic and therapeutic methods. The present invention may, for example, be used in the diagnosis and treatment of malaria. This is of topical importance because, as is well known, this disease is fast becoming resistant to current drug treatments, and, as a consequence, is becoming more prevalent throughout the world.

The functional epitope may form the basis of a diagnostic test for malaria, fungal infection, including *Pneumocystis carnii* or bacterial infection, using an immunological test such as an enzyme-linked immunosorbant assay, a radioimmunoassay or a latex agglutination assay, essentially to determine whether antibodies specific for the epitope, and therefore the particular stress protein, are present in a host organism. The test may be generally formed by contacting body fluid from the host with an epitope and detecting any complexed material.

In another use, the epitope according to the invention may be employed, using conventional techniques, for screening to obtain activity inhibiting agents for use in the treatment of malaria, fungal and bacterial infections.

In a further use, the epitope according to the invention may be used to generate antibodies, ie. for use as an immunogen, by standard techniques, for example, by injecting any suitable host with the epitope and the serum collected to yield the desired polyclonal anti-epitope antibody after purification and/or concentration. Prior to injection of the host, the epitope may be formulated in a suitable vehicle to provide a composition comprising an epitope together with one or more pharmaceutically acceptable excipients.

Alternatively, the antibodies may be monoclonal in origin and may in general belong to any immunoglobulin class, for example, IgG and/or IgM and/or IgA. The antibody may be of animal, for example, mammalian origin and may be of murine, rat or preferrably human origin, or may be a murine or rat humanised antibody.

For purification of any anti-epitope antibody, use may be made of affinity chromatography employing an immobilised epitope of the invention as the affinity medium. Such anti-epitope antibodies may be used in both the diagnosis and treatment of fungal and bacterial infections and malaria. As inhibitors of the action of a stress protein, the anti-epitope antibodies may be used either alone or in combination with other pharmaceutical agents. For example, other anti-fungal agents or anti-malarial agents. In addition, such epitopes may be used to produce other inhibitors of fungal or malarial stress proteins, for example, ribosymes and anti-sense RNA will inhibit the translation of stress protein mRNA.

A potential use of such anti-epitope antibodies is in the supportive immunotherapy of, for example, HIV positive patients. Such patients are prone to opportunistic infections due to their immune system being compromised. Examples of such opportunistic infections include Candida, Aspergillus and *Pneumocystis carnii*. Indeed, sera from HIV positive patients have been shown to be antibody positive to HSP90 of all of these organisms. It is thus proposed to provide such patients with antibody which will recognise HSP90 of these, and other infectous organisms, before these infections become establised and contribute to the death of such patients.

A particularly useful antibody according to the invention is that which recognises the peptide XXXLXVIRKXIV, or XXILXVIXXXXX, wherein X is any amino acid, for example, the peptide NKILKVIRKNIV, and an antibody which recognises one or more of the peptides KIRY, NNLGTI, QFIGYPI, KKIK, SKEQV or Candidal equivalent sequence SIKAV, GLELPE or Candidal equivalent sequence FELEES, LDKK or Candidal equivalent sequence LGDQ, WTAN or Candidal equivalent sequence WSAN, NSTMGY or Candidal equivalent sequence TTMSSY, PIVET or Candidal equivalent sequence PIIKE, or KNDK or Candidal equivalent sequence AEDK.

If desired, mixtures of antibodies may be used for diagnosis or treatment, for example mixtures of two or more antibodies recognising different epitopes of the human stress protein (or Candidal equivalent sequence), and/or mixtures of antibodies of a different class, for example, mixtures of IgG, IgM and IgA antibodies recognising the same or different epitope(s) of a human stress protein (or Candidal equivalent sequence).

The following examples illustrate the invention.

EXAMPLE 1

Possible immunodominant epitopes of the human HSP 90 have been investigated against sera from patients suffering from various types of diseases in an attempt to provide novel tools for both diagnosis and treatment of disease.

Sera examined included that from patients suffering from systemic candidiasis (47 kDa positive), invasive aspergillosis (88,40 kDa positive), allergic bronchopulmonary aspergillosis, aspergilloma, malaria, *Streptococcus faecalis* endocarditis, *Corneybacterium ieikeium* endocarditis and the autoimmune disease systemic lupus erythematosis (SLE).

Epitope mapping of human HSP 90 was carried out against the derived amino acid sequence described in Hickey et al 1989, Mol. Cell. Biol., 9, 2615–2626.

Experimental Details

The 716 amino acid residues were synthesised on polyethylene pins as a complete set of overlapping nonapeptides, in which peptide 1 consisted of residues 1–9, peptide 2 of residues 2–10, etc. Peptide synthesis was performed with Fmoc-protected amino acid esters. The polyethylene pins themselves were each coupled to Fmoc-β-alanine. After Fmoc deprotection, the first amino acid was coupled to each pin as dictated by the sequence to be synthesized. Hydrobenzotriazole-mediated coupling reactions were carried out overnight in a N,N-dimethylformamide solution of each side chain protected, Fmoc amino acid. Peptides were synthesized by successive cycles of Fmoc deprotection and addition of one amino acid per pin per day. After completion of the final coupling reaction, and removal of the Fmoc protecting group, the terminal amino group was acetylated in order to remove the unnatural charge of the N terminus of the peptide. Side chain protecting groups were removed by a mixture of trifluoroacetic acid: phenol: ethanedithiol (95: 2.5: 2.5, v/w/v).

The peptides, still coupled to the surface of the pins, were tested against sera by enzyme immunoassay (EIA). Pins were precoated for 1 hr., in microtitre plates containing 1% ovalbumin, 1% bovine serum albumin (BSA) in PBS-T (phosphate-buffered saline, 0.1% Tween 20). They were then incubated at 4° C. in patient sera (1/200) washed four times with PBS-T and incubated for 1 h with horseradish-peroxidase conjugated antiimmunoglobulin (1/1000; Sigma, Poole). After further washing, the pins were immersed for 30 min in ABTS (0.5 mg/ml amino-di-3-ethylbenzthiazoline-6-sulphonate in pH 4.0 citrate buffer with 0.03% hydrogen peroxide) and $A_{405}$ measurements made in an EIA plate reader. Pins were cleaned by sonication.

A reaction was considered to be specific if, over at least three wells, the OD was at least 2-fold above background. The large number of the peptides synthesized effectively acted as negative controls in each test. The mean absorbance of these peptides was low and was used to establish the background level (Geysen et al., 1987).

DETAILS OF PATIENT'S SERA EXAMINED

I. Disseminated Candidiasis

| Number | History |
|---|---|
| 1. | leukaemia, neutropenia, blood culture positive *C. albicans*. |
| 2. | post oesophagectomy, blood culture positive, *C. albicans*. |
| 3. | HIV positive, drug abuser, Candidal chorioretinitis. |
| 4. | Candidal peritonitis, chronic ambulatory peritoneal dialysis patient, blood culture positive *C. albicans*. |
| 5. | Post duodenal resection, positive for *C. albicans* in two sets of blood culture. |
| 6. | Pre (antibody negative), Post antibody positive. Positive for *C. alibicans* in two sets of blood culture. Post cholecystectomy. |
| 7. | Post oesophagectomy, chest drain, blood culture positive *C. albicans*. |
| 8. | *Hepatosplenic candidiasis*, yeast seen on biopsy. |
| 9. | Chronic ambulatory peritoneal dialysis patient, peritonitis, abdominal abscess, positive for *C. albicans* in two sets of blood culture. |

Antibody profile

| Case Number | *Candida albicans* | *Aspergillus fumigatus* |
|---|---|---|
| 1. | M 47, 40 KD G 47, 40 KD | NIL |
| 2. | M 47 KD G 47 KD | 88, 84 KD trace (M + G combined) |
| 3. | M 47, 48 KD G NIL | NIL |
| 4. | M 47 KD | NIL |

-continued

| Case Number | Candida albicans | Aspergillus fumigatus |
|---|---|---|
| 5. | G 47 KD<br>M 47 KD<br>G 47 KD | NIL |
| 6. | Pre NIL<br>Post M 40, 47 KD,<br>Post G 40, 47 KD | NIL |
| 7. | M 47 KD<br>G 47 KD | NIL |
| 8. | 11/12/91 NIL<br>17/1/92 M + G<br>47 KD (positive when combined) | NIL |
| 9. | M 47 KD<br>G 47 KD | 88/84 KD trace<br>(M + G combined) |

Comment

C.albicans HSP 90 has bands at 92, 47, 40 KD (as disclosed in GB 2 034 504).

A.fumigatus HSP 90 has bands at 88/84, 51 and 40 KD.

HIV positive patients sera are antibody positive for Candida HSP90, Pneumocystis carnii HSP90 and Aspergillus. Thus, it is proposed to use the antibody in maintenance therapy of such patients, since loss of antibody in these patients may lead to opportunistic infections, such as Pneumocystis carnii and other organisms which produce antigen i.e. HSP90.

II. Invasive aspergillosis

| Case Number | History |
|---|---|
| 10. | Fatal, invasive aspergiliosis, acute leukaemia |
| 11. | Fatal, invasive aspergiliosis, acute leukaemia |
| 12. | Fatal, invasive aspergiliosis, acute leukaemia |
| 13. | Survivor, invasive aspergiliosis, acute leukaemia |
| 14. | Survivor, invasive aspergiliosis, acute leukaemia |
| 15. | Survivor, invasive aspergiliosis, acute leukaemia |

Antibody Profile

| Case Number | Candida albicans | Aspergillus fumigatus |
|---|---|---|
| 10 | NIL | NIL |
| 11 | NIL | NIL |
| 12 | NIL | M 88,84 KD,<br>G 88,84 KD |
| 13 | NIL | M 88,84 KD,<br>G 88,84 KD |
| 14 | NIL | M 88,84 KD,<br>G 88,84 KD |
| 15 | NIL | M 88,84 KD,<br>G 88,84 KD |

III. Allergic bronchopulmonary aspergillosis

| Case Number | C. albicans | Aspergillus fumigatus |
|---|---|---|
| 16. | NIL | M 88,84 KD,<br>G 88,84 KD |
| 17. | NIL | M 88,84 KD,<br>G 88,84 KD |

IV. Aspergilloma

| Case Number | C. albicans | Aspergillus fumigatus |
|---|---|---|
| 18. | NIL | M 88,84 KD,<br>G 88,84 KD |

V. Streptococcus faecalis endocarditis

| 19. | C. albicans | M 47 KD<br>G 47 KD |
|---|---|---|
|  | A. fumigatus | 88, 51 KD |

The monoclonal antibody described in GB 2 034 504 crossreacts with a S.faecalis immunodominant band at 90 KD as did the rabbit serum raised against this peptide (LKVIRKNIVKKMIE-cys-KLH).

Previous work (Burnie et al. 1985) identified this antigenic band as immunodominant in S.faecalis endocarditis, suggesting that it may form the basis of a test for culture negative endocarditis.

VI. Malaria

|  | C. albicans | A. fumigatus |
|---|---|---|
| 20. | M 92 KD<br>G 47 KD | 51, 40 KD |

A further 5 cases of malaria have been immunoblotted against candidal and aspergillus extracts to show they have antibody which crossreacts with fungal HSP 90.

VII. Corynebacterium ieikeium endocarditis

|  | C. albicans | A. fumigatus |
|---|---|---|
| 21. | M 47 KD<br>G 47 KD | NIL |

VIII. Systemic lupus erythematosis (SLE)

|  | C. albicans | A. fumigatus |
|---|---|---|
| 22. | G 47 KD | NIL |
| 23. | NIL | M 88, 84 KD, G 88 KD |
| 24. | G 47, 92 KD | NIL |
| 25. | M 47 KD, G 47 KD | NIL |
| 26. | M 40, 47 KD<br>G 40, 47 KD | NIL |
| 27. | M 47 KD, G 47 KD | M 88, 84, 51, 40 KD,<br>G 88, 84, 51, 40 KD |
| 28. | NIL | NIL* |

*control serum, so that 6 SLE sera were in the experimental group (see results).

IX. C.guilliermondii meningitis/septicaemia

|  | C. albicans | A. fumigatus |
|---|---|---|
| 29. | M 40 KD, G 40 KD<br>M 47 KD, G 47 KD (trace) | NIL |

RESULTS

EPITOPE MAPPING OF HUMAN HSP 90

| Epitope | Human HSP 90 position | Sequence | Recognised by:- |
|---|---|---|---|
| 1. | 57 | KIRY | 1/3 invasive *aspergillosis* <br> 1/1 *aspergilloma* <br> 4/6 SLE sera |
| 2. | 101 | NNLGTI | 7/9 disseminated *candidiasis* 47 KDa + (including seroconversion patient*) <br> 1/1 malaria <br> 1/1 *C. quilliermondii* meningitis |
| 3. | 210 | QFIGYPI | 2/9 disseminated *candidiasis* 47 kDa + including *seroconverted patient <br> 3/3 invasive *aspergillosis* (survivors) <br> 1/2 allergic bronchopulmonary *aspergillosis* <br> 1/6 SLE sera |
| 4. | 271 | KKIK | 5/9 disseminated *candidiasis* 47 kDa + including *seroconverted patient <br> 2/3 invasive *aspergillosis* (survivors) <br> 3/3 invasive *aspergillosis* (fatal) <br> 1/1 *aspergilloma* <br> 1/4 SLE sera <br> 1/1 *S. faecalis* endocarditis |
| 5. | 404 (100% conserved *candida*) | KILKVIRK | 5/9 disseminated *candidiasis* including *seroconversion patient <br> 3/3 invasive *aspergillosis* (survivors) <br> 1/1 invasive *aspergillosis* (fatal, case no 12) <br> 1/1 malaria |
| 6. | 497 (*Candida* SIKAV) | SKEQV | 2/9 disseminated *candidiasis* <br> 3/3 invasive *aspergillosis* (survivors) <br> 1/3 invasive *aspergillosis* (fatal) <br> 1/1 *aspergilloma* <br> 3/6 SLE <br> 1/1 malaria |
| 7. | 549 (*Candida* FELEES) | GLELPE | 2/9 disseminated *candidiasis* including *seroconversion patient <br> 3/4 invasive *aspergillosis* (survivors) <br> 1/2 allergic bronchopulmonary *aspergillosis* <br> 1/1 *aspergilloma* <br> 4/6 SLE <br> 1/1 JK endorcarditis |
| 8. | 580 (*Candida* LGDO) | LDKK | 5/9 disseminated *candidiasis* <br> 1/1 invasive *aspergillosis* <br> 4/6 SLE <br> 1/1 malaria <br> 1/1 *S. faecalis* endocarditis |
| 9. | 607 (*Candida* WSAN) | WTAN | 2/9 disseminated *candidiasis* including *seroconversion patient <br> 3/3 invasive *aspergillosis* (survivors) <br> 1/1 *aspergilloma* <br> 1/1 malaria <br> 1/1 *S. faecalis* endocarditis |
| 10. | 625 | NSTMGY | 5/9 disseminated *candidiasis* including *seroconversion patient |
| | (*Candida* TTMSSY) | | 3/3 invasive *aspergillosis* (survivors) <br> 1/3 invasive *aspergillosis* (fatal) <br> 1/1 malaria <br> 1/1 *S. faecalis* endocarditis |
| 11. | 642 (*Candida* PIIKE) | PIVET | 2/3 invasive *aspergillosis* <br> 2/2 allergic bronchopulmonary *aspergillosis* <br> 3/6 SLE |
| 12. | 655 (*Candida* AEDK) | KNDK | 4/9 disseminated *candidiasis* including *seroconversion patient <br> 3/3 invasive *aspergillosis* (survivors) <br> 2/3 invasive *aspergillosis* (fatal) <br> 2/2 allergic bronchopulmonary *aspergillosis* <br> 1/1 *aspergilloma* <br> 5/6 SLE |

*seroconversion patient—refers to patient 6 whose initial serum was antibody negative, but, on subsequent recovery from the disease, tested antibody positive.

Conclusion

Epitopes 1,3,4,6,7,8,11 and 12 produced a positive response with sera from SLE patients, i.e. the epitope regognised an autoimmune antibody, and may be classed as autoantibody domains.

Epitopes 2,5,9 and 10 appear to be fungal specific, with epitope 2 being a potential candidal epitope and epitope 9 a potential aspergillosis specific epitope. In addition, epitopes 2,5,9 and 10 may be candidates for potential malarial epitopes, and epitopes 9 and 10, potential *S.faecalis* epitopes.

EXAMPLE 2

The peptide LKVIRKNIVKKMIE cys was used to raise the monoclonal sera used in GB 2 034 504. However, the detailed immunogenicity of this peptide is unknown. It was decided to investigate this by replacing each of the amino acids in the above peptide to see the effect, if any, on immunogenicity.

The necessary peptides were first synthesised using conventional techniques and immunogenicity measured using the human sera containing the monoclonal antibody described above. It was also decided to examine a wide epitope, namely NKILKVIRKNIV.

The protocols and antibody concentrations were the same as those described above in Example 1.

Peptides evaluated

| Peptide 1 | LKVIRKNIV <br> evaluated for changes in LKVIRK |
|---|---|
| Peptide 2 | NKILKVIRK <br> evaluated for changes in KILK |
| Peptide 3 | LKVIRKNIV <br> evaluated for changes in KNIV |

So that in the total sequence the

```
N K I L K  V I R  K  N I V
     └───┘        └─┘
```

| Peptide | 2 | 1 | 3 | changes were examined |

Sera assayed

1. Monoclonal specfifc to LKVIRKNIVKKMIE - cys against peptides 1 and 3.
2. Human sera.

| Patient Number | Sera | Diagnosis |
|---|---|---|
| 2 | single | Post oesophagectomy, blood culture positive C. albicans. |
| 6 | paired* | Post cholecystectomy, blood culture positive C. albicans in two sets of blood culture. |
| 30 | paired* | Neutropenia, leukaemia, blood culture positive C. tropicalis in three sets of blood culture. |
| 31 | paired* | Neutropenia, leukaemia, blood culture positive C. parapsilosis in two sets of blood culture. |
| 16 | paired* | Survivor, invasive aspergiliosis acute leukaemia. |
| 33 | single | P. vivax malaria |
| 34 | single | P. falciparum malaria |
| 35 | single | P. falciparum malaria |
| 20 | single | P.vivax malaria |
| 24 | single | SLE |

*paired means that there is an early serum which was antibody negative which is compared to an antibody positive second serum.

ANTIBODY PROFILES

| Patient No. | C. albicans | A. fumigatus |
|---|---|---|
| 2 | M 47 KD, G 47 KD | M/G 88,84 KD (trace) combined |
| 6 Post serum | M 40, 47 KD, G 40, 47 KD | NIL |
| 30 Post serum | M 47 KD, G 47 KD | NIL |
| 31 Post serum | M 47 KD, G 47 KD | G 40 KD |
| 16 | NIL | M 88, 84 KD, G 88, 84 KD |
| 33 | M 47 KD, G 47 KD | NIL |
| 34 | M 92, 47 KD, G 47 KD | G 88 KD |
| 35 | M 47 KD | NIL |
| 20 | M 92 KD, G 47 KD | G 51, 40 KD |
| 24 | G 47 KD | NIL |

Results:

1. Monoclonal specific to LKVIRKNIVKKMIE—cys

Peptide 1—LKVIRKNIV

ELISA values measured at 30 minutes, antibody dilution 1:200

Control LKVIRKNIV average ELISA OD=0.923 (controls)

Substituted amino acid

| | (resultant OD) | | | | | |
|---|---|---|---|---|---|---|
| | L | K | V | I | R | K |
| A | 0.875 | 1.102 | 0.594 | 0.526 | 0.111 | 0.132 |
| C | 0.849 | 0.797 | 0.527 | 0.324 | 0.125 | 0.119 |
| D | 0.909 | 1.208 | 0.730 | 0.195 | 0.126 | 0.138 |
| E | 1.005 | 1.183 | 1.021 | 0.977 | 0.141 | 0.135 |
| F | 1.052 | 0.760 | 0.512 | 0.483 | 0.116 | 0.108 |
| G | 0.054 | 1.016 | 0.525 | 0.161 | 0.131 | 0.133 |
| H | 0.798 | 0.926 | 0.905 | 0.454 | 0.107 | 0.190 |
| I | 1.021 | 0.714 | 0.491 | control | 0.117 | 0.12 |
| K | 0.392 | control | 0.881 | 0.486 | 0.092 | control |
| L | control | 0.946 | 0.673 | 0.659 | 0.122 | 0.114 |
| M | 0.836 | 1.075 | 0.508 | 0.715 | 0.118 | 0.364 |
| N | 0.764 | 1.223 | 0.769 | 0.306 | 0.124 | 0.137 |
| P | 0.77 | 0.662 | 0.612 | 0.489 | 0.095 | 0.132 |
| Q | 0.656 | 1.073 | 0.813 | 0.602 | 0.120 | 0.231 |
| R | 0.668 | 1.032 | 0.657 | 0.538 | control | 0.591 |
| S | 0.500 | 1.026 | 0.620 | 0.434 | 0.121 | 0.146 |
| T | 0.693 | 0.944 | 0.740 | 0.760 | 0.127 | 0.139 |
| V | 0.788 | 0.799 | control | 0.977 | 0.126 | 0.124 |
| W | 1.022 | 0.991 | 1.082 | 0.895 | 0.104 | 0.115 |
| Y | 0.584 | 1.007 | 1.196 | 0.788 | 0.110 | 0.119 |
| | (L) | (K) | (V) | (I) | (R) | (K) |

These results show the importance of the amino acids IRK, with RK being irreplaceable, antibody binding being negligible upon subsitution of these amino acids.

Peptide 3—LKVIRKNIV

ELISA values measured at 30 minutes, antibody dilution 1:200

Control LKVIRKNIV average ELISA OD=0.842

| | K | N | I | V |
|---|---|---|---|---|
| A | 0.101 | 0.615 | 0.109 | 0.134 |
| C | 0.105 | 0.196 | 0.122 | 0.148 |
| D | 0.100 | 0.344 | 0.100 | 0.120 |
| G | 0.102 | 0.446 | 0.101 | 0.113 |
| F | 0.101 | 0.166 | 0.142 | 0.456 |
| G | 0.099 | 0.331 | 0.100 | 0.124 |
| H | 0.107 | 0.655 | 0.114 | 0.123 |
| I | 0.100 | 0.169 | control | 0.938 |
| K | control | 0.746 | 0.095 | 0.136 |
| L | 0.103 | 0.248 | 0.268 | 0.831 |
| M | 0.099 | 0.630 | 0.283 | 0.430 |
| N | 0.101 | control | 0.103 | 0.107 |
| P | 0.101 | 0.247 | 0.107 | 0.095 |
| Q | 0.103 | 0.596 | 0.103 | 0.112 |
| R | 0.192 | 0.819 | 0.105 | 0.121 |
| S | 0.104 | 0.942 | 0.127 | 0.128 |
| T | 0.101 | 0.691 | 0.181 | 0.227 |
| V | 0.100 | 0.210 | 0.765 | control |
| W | 0.098 | 0.139 | 0.106 | 0.123 |
| Y | 0.102 | 0.145 | 0.107 | 0.105 |

These results show the importance of amino acids KNIV.

The total epitope is I R K N I V with the underlined amino acids virtually impossible to replace.

2. Human Sera

All ELISA performed combined IgM and IgG at 30 minutes. Antibody dilution 1:200

Peptide 1

| Patient Number | Average ELISA | Number of amino acids giving a reduction to a maximum of 70% control | | | | | |
|---|---|---|---|---|---|---|---|
| | | L | K | V | I | R | K |
| 2 | 1.01 | 14 | 4 | 14 | 16 | 5 | 8 |
| 6 Pre | 0.1 | not applicable | | | | | |
| Post | 0.501 | 16 | 9 | 16 | 15 | 4 | 3 |
| 30 Pre | 0.22 | not applicable | | | | | |
| Post | 0.752 | 9 | 0 | 11 | 15 | 2 | 1 |
| 31 Pre | 0.1 | not applicable | | | | | |
| Post | 0.648 | 14 | 0 | 15 | 17 | 4 | 0 |
| 16 Pre | 0.347 | not applicable | | | | | |
| Post | 0.647 | 10 | 2 | 17 | 12 | 2 | 0 |
| 33 | 1.18 | 6 | 1 | 12 | 15 | 2 | 0 |
| 34* | 0.6 | 12 | 0 | 6 | 6 | 0 | 0 |
| 35 | 1.24 | 8 | 2 | 7 | 7 | 2 | 2 |
| 20 | 1.3 | 10 | 1 | 8 | 8 | 1 | 1 |
| 24 | 0.379 | not applicable | | | | | |

*serum examined at 1:1000 dilution. where ELISA readings were below 0.4, these results were deemed not applicable as they were around the background level.

Peptide 2

| Patient Number | Average ELISA | Number of amino acids giving a reduction to a maximum of 70% control | | | |
|---|---|---|---|---|---|
| | | K | I | L | K |
| 2 | 1.37 | 8 | 19 | 19 | 8 |
| 6 Pre | 0.10 | not applicable | | | |
| Post | 0.33 | not applicable | | | |
| 30 Pre | 0.22 | not applicable | | | |
| Post | 1.62 | 10 | 18 | 17 | 1 |
| 31 Pre | 0.11 | not applicable | | | |
| Post | 0.58 | 10 | 18 | 17 | 3 |
| 16 Pre | 0.3115 | not applicable | | | |
| Post | 0.531 | 2 | 17 | 14 | 13 |
| 33 | | 7 | 16 | 12 | 2 |
| 34* | 0.47 | 4 | 17 | 16 | 2 |
| 35 | 1.36 | 10 | 18 | 17 | 3 |
| 20 | 1.2 | 8 | 16 | 16 | 2 |
| 24 | 0.32 | not applicable | | | |

*serum examined at 1:1000 ELISA values less than 0.4 taken as background, therefore deemed not applicable.

Peptide 3

| Patient Number | Average ELISA | Number of amino acids giving a reduction to a maximum of 70% control | | | |
|---|---|---|---|---|---|
| | | K | N | I | V |
| 2 | 0.89 | 0 | 0 | 0 | 0 |
| 6 Pre | 0.01 | not applicable | | | |
| Post | 0.438 | 0 | 0 | 0 | 0 |
| 30 Pre | 0.2 | not applicable | | | |
| Post | 0.52 | 0 | 0 | 3 | 3 |
| 31 Pre | 0.35 | not applicable | | | |
| Post | 0.66 | 0 | 1 | 9 | 4 |
| 16 Pre | 0.3 | not applicable | | | |
| Post | 0.59 | 3 | 8 | 15 | 11 |
| 33 | 1.03 | 1 | 13 | 11 | 7 |
| 34* | 0.566 | 3 | 15 | 14 | 12 |
| 35 | 1.437 | 0 | 8 | 10 | 3 |
| 20 | 1.18 | 8 | 14 | 15 | 15 |
| 24 | 0.37 | not applicable | | | |

*serum examined at 1:1000 ELISA values less than 0.4 taken as background, therefore deemed not applicable.

EXAMPLE 3

A library of immunoglobulin heavy and light chain variable (V) genes was prepared from the peripheral blood lymphocytes of a patient who had recovered from systemic candidiasis. The library was enriched and screened for activity to LKVIRKNIVKKMIE and NKILKVIRKNIVKK and the resulting human recombinant antibodies examined for therapeutic activity in a mouse model of systemic candidiasis.

Experimental Details

The library was produced essentially as described by Marks et al (J Mol Biol 1991; 222: 581–597) using the pCANTAB 5 vector, which is now commercially available as part of a kit from Pharmacia (Milton Keynes, UK). The heavy and light chain V genes, obtained from cDNA prepared from the mRNA of peripheral blood lymphocytes of a patient recovering from systemic candidiasis, were randomly combined and subcloned into Not I/Sfi I digested pCANTAB 5. The resulting single chain Fv fragments (ScFv), expressed on the surface of phage, were enriched by panning against specific synthetic peptide epitopes, including LKVIRKNIVKKMIE and NKILKVIRKNIVKK. Then immunoblotting (see Example 4) was used to identify individual clones with activity against the 47 kd antigen of Candida albicans. Two strongly positive recombinant antibodies were selected for further study: A2 (panned against LKVIRKNIVKKMIE) and B3 (panned against NKILKVIRKNIVKK).

Female Balb/c mice were injected intravenously with a lethal dose of Candida albicans. Two different age groups were examined - mature mice weighing around 20 g (experiments 1 and 2) and young mice weighing around 12 g. Two different batches of human recombinant B were examined (experiment No. 1 against No's 2 and 3). In experiment 1 this recombinant antibody was compared against human recombinant antibody A and helper phage M13 K07, and 200 µl of saline, M13 K07 or human recombinant antibody was given approximately 2 hours after iv challenge with Candida. In experiments 2 and 3, 100 ul of saline or B3 was given 1 hours after iv challenge with Candida.

Results

| Expt. No. | CFU | Av.Wt. of mice (g) | Treatment Group (No. of mice) | % mortality at 24 h (No. dead) |
|---|---|---|---|---|
| 1 | 10⁸ | 21 ± 3 g | Saline (11) | 73% (8) |
| | 10⁸ | 21 ± 3 g | M13K07 (17) | 76% (13) |
| | 10⁸ | 21 ± 3 g | A (16) | 94% (15) |
| | 10⁸ | 21 ± 3 g | B (10) | 10% (1) |
| 2 | 10⁷ | 19 ± 2 g | Saline (10) | 40% (4) |
| | 10⁷ | 19 ± 2 g | B (10) | 10% (1) |
| 3 | 10⁸ | 12 ± 2 g | Saline (16) | 25% (4) |
| | 10⁷ | 19 ± 2 g | B (16) | 0% (0) |

Comment

Younger mice appear to be relatively resistant to Candida albicans (an analogous situation occurs in humans). Human recombinant antibody B repeatedly showed therapeutic activity against Candida—unlike human recombinant antibody A.

EXAMPLE 4

Human recombinant antibodies B3 and A2 were examined for cross-reactivity against Streptococcus faecalis and Corynebacterium jeikeium.

Experimental details

Immunoblots of *Candida albicans*, *Corynebacterium jeikeium* and *Streptococcus faecalis* were prepared as previously described (Matthews, Epidemiol. Infect. 1991; 107: 273–283; Burnie et al, J. Clin. Path. 1987; 40: 1149–1158). Free-protein binding sites were blocked with bovine serum albumin (BSA), prior to incubating each blot with the phage suspension (B3 or A2) for 2 hours at room temperature, with gentle agitation. They were then washed five times over 30 min in 0.05% Tween 20-Saline, and incubated for 90 minutes with anti-M13 antibody (commercially available from 5'-3', Inc. Boulder, USA), diluted 1:1000 in 3% BSA. Washing was repeated and then they were incubated with alkaline-phosphase conjugated anti-goat antibody (diluted 1:1000), from Sigma, for 1 hours. Washing was repeated and then the blots were developed with the colour substrate BCIP NBT as previously described (Matthews 1991).

Results

B3 and, to a less extent, A2, cross-reacted with *Streptococcus faecalis* and *Corynebacterium jeikeium* as well as *Candida albicans*. Several bands were produced. In the case of *S.faecalis* these were at about 112 kd, 88–90 kd and 32 kd. In the case of *C.jeikeium* bands occurred at about 160 kd, 52 kd, 47 kd and 40 kd. In the case of *C.albicans* a Prominent band occurred at 47 kd.

Comments

Human recombinant antibodies B3 and A2 cross-reacted with *S.faecalis* and *C.jeikeium* and may have therapeutic potential against these and other Grampositive bacteria.

EXAMPLE 5
Dot—Immunobinding Assay
Material and Methods

1 µl of human serum was dotted onto a sheet of nitrocellulose membrane (Biorad Laboratories, California). This was allowed to dry for 10 minutes. It was blocked for 1 hour at 37° C. with 3% Bovine Serum Albumen in Tris-buffered saline pH 7.5. After being washed in 0.9%/weight/volume/saline—0.05% Tween 80 five times over 30 minutes it was incubated for 1 hour at room temperature with the human recombinant antibody B3 diluted 1 in 5. It was then washed for 30 minutes, as described above, and further incubated with the anti-M13 horseradish peroxidase conjugate (Pharmacia Ltd), diluted 1 in 5,000 in 3% bovine serum albumin in Tris-buffered saline. After a further wash, this was developed with the 3-amino-9-ethylcarbazole substrate (0.67 ml of a solution of 0.4 gram 3-amino-9-ethylcarbazole/100 ml dimethyl formamide in 10 mls of 0.1M sodium acetate (pH 5.2)). This was activated with 10 µl of 30% $H_2O_2.H_2O_2$. The blot was incubated for 30 minutes and washed. The results were compared with a positive control of 1 µl of candidal pressate (100 mg/ml) and graded as negative (nil), weakly positve (trace) and positive (equivalent to the result from the candidal extract).

Dot Immunobinding Assay with Recombinant Antibodies Results

Control sera (sera from patients with no evidence of disseminated or oral candida, either with leukaemia or after major gastrointestinal surgery).

| Titre: | NIL | Trace | Positive |
|---|---|---|---|
| No. of Sera: | 79 | 2 | NIL |

The two trace positive patients came from a group of five with an underlieing septicaemia due to a *Corynebacterium jeikeium*.

Colonized Patients (sera from patients with a colonized site either oral/wound/vaginal/intraveneous line/urine).

| Titre | NIL | Trace | Positive |
|---|---|---|---|
| Oral | 6 | 1 | |
| Wound | 1 | | |
| Vaginal | 1 | | |
| Intravenous | 3[a] | | |
| Urine | 2 | | 1[b] |

[a] includes 1 case of *C.parapsiliosis* colonization
[b] required treatment Amphotericin B.

Systemic patients

Defined as either (1) two sets of positive blood cultures taken at least 24 hours apart from two different intravenous sites or (2) cultural and histopathological evidence obtained at postmortem.

Each patient is reported as the maximum antigen titre detected if a series of samples was available.

| | Maximum Antigen Titre Detected | | |
|---|---|---|---|
| Causative yeast | Nil | Trace | Positive |
| *Candida tropicalis* | 1 | 1 | |
| *Torulopsis glabrata* | | | 1 |
| *Candida parapsilosis* | | | 1 |
| *Candida albicans* | 2 | 3 | 17 |

Comments

Antigen detected by dot immunobinding with the B3 recombinant antibody distinguished control sera and sera from colonized patients from the sera of patients with systemic candidiasis.

CONCLUSIONS
Concerning heat shock protein epitopes

The amino acids underlined below are vital, i.e. irreplaceable, to the function of the epitope as an immunogen. In addition, sera of patients with different diseases produce antibodies which recognise slightly different amino acids within the same epitope.

Case 24, an SLE patient acted as a positive control, as, although this patients sera was positive for the candidal 47 KD protein, it did not recognise any of the 3 peptides of the epitope of the present invention.

| | | | |
|---|---|---|---|
| Monoclonal epitope | | L K V I R K N I V | |
| *C. albicans* epitope | case 2 | N K IL K VI R K N I V | |
| | case 6 | N K IL K VI R K N I V | |
| *C. tropicalis* | case 30 | N K IL K VI R K N I V | |
| *C. parapsilosis* | case 31 | N K IL K VI R K N I V | |
| *A. fumigatus* | case 16 | N K IL K VI R K N I V | |
| Malaria:. vivax | case 33 | N K IL K VI R K N I V | |
| | case 20 | N K IL K V I R K N I V | |
| falciparum | case 34 | N K IL K VI R K N I V | |
| | case 35 | N K IL K V I R K N I V | |

The monoclonal described in GB 2 034 504 reacts with an epitope which only represents part of the epitope for yeast infection (*C.albicans/C.tropicalis/ C.parapsilosis*). Infections due to *C.tropicalis*, *A.fumigatus* and malaria are more immunoreactive to the KILK epitope. Infections due to malaria and *A.fumigatus* also recognise an epitope containing NIV.

Thus a more active antibody recognising stress proteins produced in a wider range of diseases than that described in GB 2 034 504 may be produced against the epitope N K I L K V I R K N I V (i.e. antibody B3).

Concerning antibodies against heat shock protein epitopes

The data demonstrate that antibodies raised against X X X L X V I R K X I V and/or X X I L X V I X X X X X, where X is any amino acid, particularly human recombinant antibodies, show protection in the mouse model of systemic candidiasis.

It will be appreciated that it is not intended to limit the invention to the above examples only, many variations, such as might readily occur to one skilled in the art, being possible, without departing from the scope thereof as defined by the appended claims.

We claim:

1. An isolated epitope of up to nine amino acids from human HSP90 which cross-reacts with an antibody against at least one other HSP90 protein, said epitope comprising the amino acid sequence Lys Ile Arg Tyr or Asn Asn Leu Gly Thr Ile.

2. An epitope according to claim 1, wherein the HSP90 protein comprises a malarial stress protein.

3. An epitope according to claim 1, wherein the HSP90 protein comprises a fungal stress protein.

4. An epitope according to claim 1, wherein the HSP90 protein comprises a bacterial stress protein.

5. An epitope according to claim 3, wherein the fungal stress protein comprises a protein selected from the group consisting of a Candidal 92 and 47 KDa proteins.

6. An epitope according to claim 3, wherein the fungal stress protein comprises a protein selected from the group consisting of Aspergillus 40, 51 and 88/84 proteins.

7. An epitope according to claim 3, wherein the fungal stress protein comprises a Pneumocystis carinii protein.

8. An epitope according to claim 4, wherein the bacterial stress protein comprises a Streptococci 90 KD stress protein.

9. An epitope according to claim 4, wherein the bacterial stress protein comprises a Corynebacterial 86 KD or Corynebacterial 52 KD or Corynebacterial 86 and 52 KD stress protein.

10. A diagnostic kit comprising an epitope according to claim 1 and instructions for performing a diagnostic test.

11. A diagnostic kit according to claim 10, wherein the diagnostic test is a dot immunosorbent assay, a radioimmunoassay or a latex agglutination assay.

12. An isolated epitope of up to nine amino acids from human HSP90 which cross-reacts with an antibody raised against at least one of the HSP90 proteins of Candida, *Streptococcus faecalis, Corynebacterium jeikeium, Aspergillus fumigatus, Plasmodium vivax and Plasmodium falciparum*, wherein said epitope comprises the amino acid sequence Lys Ile Arg Tyr or Asn Asn Leu Gly Thr Ile.

* * * * *